(12) United States Patent  
Martin et al.

(10) Patent No.: US 9,274,432 B2  
(45) Date of Patent: Mar. 1, 2016

(54) SELECTIVE MASKING BY PHOTOLITHOGRAPHY (SMP) FOR MAKING ELECTROCHEMICAL MEASUREMENTS

(75) Inventors: Farrel Martin, Waldorf, MD (US); Alberto Piqué, Crofton, MD (US); Raymond C Y Auyeung, Alexandria, VA (US); Steve Policastro, Waldorf, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 314 days.

(21) Appl. No.: 13/618,214

(22) Filed: Sep. 14, 2012

(65) Prior Publication Data

US 2013/0248382 A1 Sep. 26, 2013

Related U.S. Application Data

(60) Provisional application No. 61/540,093, filed on Sep. 28, 2011.

(51) Int. Cl.
*G03F 7/20* (2006.01)
*G03F 7/26* (2006.01)

(52) U.S. Cl.
CPC ............ *G03F 7/2002* (2013.01); *G03F 7/2053* (2013.01); *G03F 7/26* (2013.01); *Y10T 428/13* (2015.01)

(58) Field of Classification Search
CPC ........ G03F 7/2002; G03F 7/2053; G03F 7/26
USPC .................................. 430/22, 311, 313, 327
See application file for complete search history.

(56) References Cited

U.S. PATENT DOCUMENTS

| | | | |
|---|---|---|---|
| 7,989,148 B2 * | 8/2011 | Nakashiba et al. ........... | 430/318 |
| 2002/0097440 A1 * | 7/2002 | Paricio ......................... | 358/3.29 |
| 2011/0076843 A1 * | 3/2011 | Huang et al. .................. | 438/585 |
| 2013/0003032 A1 * | 1/2013 | Jain ................................. | 355/67 |

OTHER PUBLICATIONS

Policastro, S.A.; An Approach for Determining Microscale Electrochemical Behavior; J. Electrochem. Soc. 2012 vol. 159, issue 1, C15-C24.

Policastro, S.A.; Isolating the Electrochemical Behavior of the Austenite and Ferrite Phases in a Duplex Stainless Steel; ECS Transactions, 25 (37) 133-153 (2010).

* cited by examiner

*Primary Examiner* — Kathleen Duda
(74) *Attorney, Agent, or Firm* — US Naval Research Laboratory; Stephen T. Hunnius

(57) ABSTRACT

A method for isolating microstructural regions or features on a surface for electrochemical experimentation comprising polishing a metal sample, coating the metal sample with a photoresist, selecting a region of interest of the metal sample, exposing the region of interest with light energy, developing the exposed photoresist and creating a developed region.

14 Claims, 3 Drawing Sheets

SELECTIVE MASKING BY PHOTOLITHOGRAPHY (SMP) FOR MAKING ELECTROCHEMICAL MEASUREMENTS

This application claims priority to and benefit of U.S. Patent Application No. 61/540,093 filed Sep. 28, 2011, the entirety of which is herein incorporated by reference.

BACKGROUND

This procedure provides a technique for conducting electrochemical experiments on precise microstructural features on a material surface. This procedure furthermore minimizes loss of signal due to high solution resistance.

Earlier procedures suffer from several disadvantages. Examples include microcapillaries and lacquers. Microcapillaries have the disadvantages of high solution resistance through the capillary, solution leakage at the seal with the sample surface, and imprecise capillary placement.

Using lacquers is a technique that was suggested in the 1970s and consisted of coating the surface to be sampled with a lacquer and then to make small pinholes over the regions to be investigated. Again, the use of lacquers as a technique suffers from several disadvantages.

One of the challenges associated with electrochemical testing is that it is difficult to determine individual contributions to a measured current especially when the sample area comprises multiple grains, grain boundaries, precipitates, etc. The heterogeneity of such areas result in competing kinetic processes that contribute to the overall current.

For studies that are aimed at determination for example, of corrosion resistance or catalytic activity, it would be beneficial to have a versatile technique that can isolate areas of interest.

Localized experimental procedures using micro-capillaries (1-3) to probe small areas of the sample surfaces have been developed previously. Though the micro-capillary technique has been in widespread use for the past 15 years, aspects of the technique make it undesirable for certain experimental procedures. For example, the relatively fast potentiodynamic sweep rates required to prevent cell leakage or tip blockage of the micro-capillary prevent scanning at rates as slow as 10 mV/min and the micro-capillary tip diameter can affect the limiting current passing through the cell. In addition a flat, polished surface is needed for this technique.

Here, a technique for making electrochemical measurements on isolated individual phase regions of known crystalline orientation in a duplex stainless steel is demonstrated. An ultraviolet-sensitive photoresist is used to mask the excluded portions of the sample and a 355 nm laser exposes only portions of the ferrite matrix or cross-sections of austenite dendrites. Initial impedance measurements indicate a relatively low solution resistance in seawater and the polarization scans of the ferrite and austenite phases were consistent with bulk polarization measurements.

BRIEF SUMMARY OF THE INVENTION

This procedure provides a technique for conducting electrochemical experiments on precise microstructural features on a material surface.

This procedure furthermore minimizes loss of signal due to high solution resistance.

This disclosure describes and demonstrates the utility and viability of a novel experimental technique, Selective Masking by Photolithography (SMP), for making electrochemical measurements on individual phase or isolated regions of an alloy. Here, a technique for making electrochemical measurements on isolated individual phase regions of known crystalline orientation in a duplex stainless steel is demonstrated. An ultraviolet-sensitive photoresist is used to mask the excluded portions of the sample and a 355 nm laser exposes only portions of the ferrite matrix or cross-sections of austenite dendrites.

In this disclosure, the technique was used to isolate individual ferrite and austenite phases from their neighbors on a polished duplex stainless steel sample (alloy 2205). Alloy 2205, UNS S32205, is a corrosion resistant alloy that consists of approximately equal amounts of $\delta$-ferrite and $\gamma$-austenite phases.

Polarization scans, electrochemical impedance, and critical pitting temperature experiments were then performed on these isolated regions.

This novel technique for making electrochemical measurements on individual phase or isolated regions of a metal or alloy is disclosed. The technique, called Selective Masking by Photolithography (SMP), uses a hardened photoresist coating to mask the excluded portions of the sample and 355 nm laser pulses are employed to expose individual grains or regions of interest. The size of the exposed area can range from tens of microns to millimeters. Localized electrochemical DC and AC measurements and critical pitting temperature determinations for the two phases in a duplex stainless steel were used to show the utility and viability of SMP.

DETAILED DESCRIPTION

Figure 1:
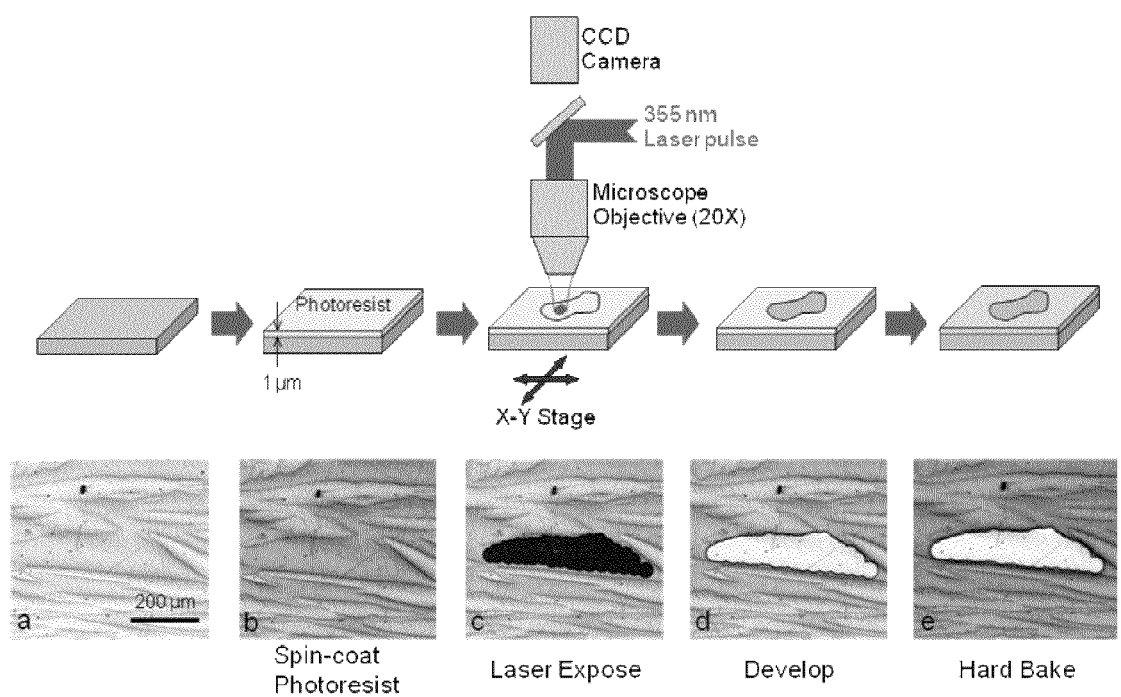
FIG. 1 is a schematic diagram of the procedure used to expose and isolate individual phases and the corresponding images of each step for a ferrite region of a 2205 steel sample. In a) is shown the image with the scale of 200 μm. A green (UV blocking) filter is used in b) and c) to prevent light emission from the microscope illuminator from further exposing the photoresist. In d) is shown the image of the develop step and in e) is shown the image of the hard bake step.
Figure 2:
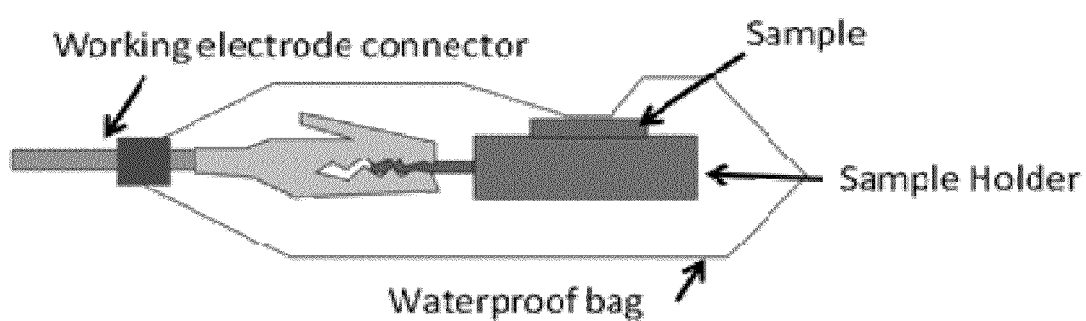
FIG. 2 illustrates the set-up for providing a conducting path for the electrons to and from the active surface and how the set-up was electrically shielded from the electrolyte.
Figure 3:
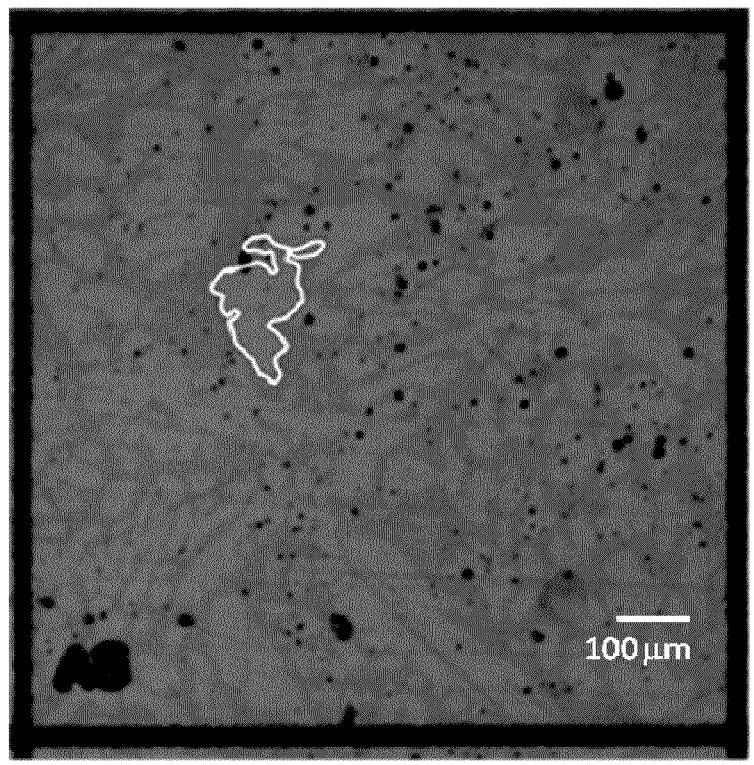
FIG. 3 is an optical microscopy image of an austenite region of interest that will be uncovered via ultraviolet exposure of the insulating photoresist.

This procedure provides a technique for conducting electrochemical experiments on precise microstructural features on a material surface.

This procedure furthermore minimizes loss of signal due to high solution resistance.

This disclosure describes and demonstrates the utility and viability of a novel experimental technique, Selective Masking by Photolithography (SMP), for making electrochemical measurements on individual phase or isolated regions of an alloy.

In this disclosure, the technique was used to isolate individual ferrite and austenite phases from their neighbors on a polished duplex stainless steel sample (alloy 2205). Alloy 2205, UNS S32205, is a corrosion resistant alloy that consists of approximately equal amounts of $\delta$-ferrite and $\gamma$-austenite phases.

In another embodiment of this invention, any light source that is coherent (laser) or incoherent (lamp) may be used to selectively expose regions of interest on the photoresist layer applied on the surface of a sample. The light source can be pulsed or continuous (cw) in nature. In the case of positive (negative) photoresist material, the regions of interest could be removed (remain) after light exposure and subsequent developing of the photoresist layer. In addition, the spatial light distribution from the light source could be spatially modulated and shaped to select the regions of interest on the photoresist layer. The shaping of the light distribution could be accomplished by transmitting the light energy (power) through a shadow mask placed near the photoresist layer, or by imaging a desired spatial light distribution through an imaging mask onto the photoresist layer, or by direct modulation of the light distribution itself by optoelectronic devices such as spatial light modulators or digital micromirror devices.

Polarization scans, electrochemical impedance, and critical pitting temperature experiments were then performed on these isolated regions. In this work, the sample surfaces were flat and polished but the technique could be used to study irregular surfaces.

Although the application for this work is related to corrosion, SMP has wide applicability to any electrochemical study that explores the behavior of individual phase or isolated regions of interest.

EXAMPLE 1

Sample Preparation was conducted as follows.

Duplex stainless-steel 2205 cast samples were provided by Wärtsilä. The phase compositions were determined via the energy dispersive x-ray spectroscopy (EDS) probe on a LEO 1550 Scanning Electron Microscope (SEM). The measured compositions are shown in Table 1.

TABLE 1

Composition (atomic %) of the δ and γ phases in
the 2205 samples - as determined using EDS.

| Phase | Fe | Cr | Ni | Mo | Mn | Si | C |
|---|---|---|---|---|---|---|---|
| γ-Austenite | 66.48 | 22.16 | 6.71 | 1.43 | 1.24 | 1.98 | 0.18 |
| δ-Ferrite | 63.95 | 23.89 | 4.38 | 3.83 | 0.84 | 1.12 | 0.18 |

The metal samples were machined to 19 mm×19 mm×2 mm coupons and polished by hand through 1200 grit sandpaper then mechanically polished using 0.05 micron alumina for up to 18 hours on a vibratory polisher.

A 10×10 square grid composed of 1 mm squares was laser machined onto the surface using a pulsed ultraviolet laser in order to provide reference marks for locating regions of interest to be tested.

The next step in the process for performing electrochemical measurements of specific phase regions required identifying the different phases and regions of interest on the surface of the sample.

Optical microscopy provided sufficient contrast between the austenite phase and ferrite matrix on the surface and therefore was used for much of the initial screening of the 2205 samples. However, in cases in which the crystalline orientation needed to be known, the screening process was done from crystalline orientation maps obtained from electron backscatter diffraction (EBSD) scans.

A next step in the procedure was the isolation of these selected phase regions using the SMP technique.

This technique is based on laser lithography—a well-established direct-patterning technique that avoids the complexity and cost of mask fabrication.

An UV (355 nm) solid state (Nd:YVO4) laser (Spectra-Physics YHP40) with maximum pulse energies of ~300 µJ and pulsewidths of ~30 ns (FWHM) was used as the laser source and the laser/motion-control system was utilized.

A 1 µm-thick layer of Microposit S1818 photoresist was spin-coated onto the sample surface and soft-baked at 110° C. for 1-2 min on a hot plate.

The areas of interest were then mapped by translating the sample on a high-resolution (10 nm) X-Y stage as it was exposed to individual 355 nm laser pulses that were focused through a 20× microscope objective into approximately 40 µm diameter spots on the sample surface.

The energy of the laser spot was measured to be ~2.6 µJ corresponding to a fluence of ~200 mJ/cm$^2$ on the surface, which did not damage the steel, but was sufficient to expose the photoresist.

After exposure, the sample was immersed in a developer solution (Microposit MF-319) which removed the photoresist coating to reveal the bare steel surface of these selected regions while the rest of the surface was still protected by the unexposed photoresist.

The sample was then hard-baked at 150° C. for 60 minutes to improve the coating reliability and adhesion during corrosion testing.

Multiple 'windows' were opened on the surface coating and were robust enough to allow several corrosion experiments to be performed on the same sample. FIG. 1 illustrates the laser lithography process on the sample.

EXAMPLE 2

Electrochemical measurements were conducted.

Each photoresist-coated sample had multiple windows emplaced over various phase regions, so a procedure was developed to electrically isolate the sample and the other windows so that only a single phase region or boundary was exposed to the electrolyte.

A small hole-punch (approximately 3 mm in diameter) was used to create a window in the Kapton polymide tape that would isolate the window of interest from the surrounding grids. Kapton polymide tape was chosen because its adhesive properties did not damage the photoresist coating between repeated application and removal.

A zip-lip, 2"×3", 2 mil thick polyethylene bag was used to provide electrical isolation from the electrolyte. A hole was cut into the bag using a brass cutter that was larger than the Kapton tape window and the edges of the hole were sealed using Scotch Brand 1280 EMP electroplater's tape.

The electrolyte used for all of the experiments was natural seawater. The seawater was pasteurized at 65° C. for a minimum of 12 hours prior to use. All of the electrochemical experiments were conducted in room temperature solutions.

Polarization scans that were performed in a deaerated environment were obtained by bubbling argon gas into the sealed cell.

EXAMPLE 3

The experiments were divided into two sets. The first set consisted of proof-of-concept tests to determine the procedure that would be followed and to establish baseline measurements of the properties of the material. The second set of experiments was designed to explore the effect of temperature on pitting corrosion in austenite and ferrite and to measure the characteristics of the oxide films that formed over the austenite and ferrite using electrochemical impedance spectroscopy.

EXAMPLE 4

Baseline Measurements

For comparison to the individual grain experiments and to test the preparation procedure for a 0.005 cm² portion of one of the grid cells was exposed by the laser and tested in aerated seawater.

The current density from the exposed region ranged from $10^{-7}$ to $\sim 10^{-6}$ A/cm² as the potential was increased from −0.5 to 1.0 $V_{SCE}$.

Two other samples were selectively etched using a combination of aggressive solution chemistries and potentiostatic holds at potentials that corresponded to the active corrosion peaks for each phase. This selective etching process removed either the ferrite or austenite grains depending on the potential.

These samples were then coated with the photoresist and lightly polished using 600 grit silicon carbide to remove the photoresist from the unetched phase.

Thus the electrochemical behavior of a high surface area of either the austenite or ferrite could be obtained and compared to the response from samples prepared using SMP. These bulk exposed ferrite and austenite samples were also tested in aerated seawater.

EXAMPLE 5

Solution Resistance and Impedance Measurements

As detailed in the following section, making electrochemical measurements on such small areas of exposed metal presented several challenges to ensure that valid measurements were being obtained. For example, one of our concerns was that solution resistance, due to current crowding in the vicinity of the exposed region of the photoresist, would affect measurements.

To evaluate the magnitudes of the solution and polarization resistances, we performed impedance measurements on exposed austenite and ferrite regions that had been held at their open-circuit potential for two hours in aerated seawater.

The solution resistance between the exposed region and the reference electrode for samples with areas on the order of $10^{-4}$ cm² was measured to be 515Ω=0.206 Ω·cm² from the Nyquist plots. An adjusted polarization scan showing the corrected potential applied to the interface as compared to the measured values was demonstrated.

The similarity between the two plots indicates that the ohmic IR drop between the sample and the reference electrode is negligible in polarization scans done on the regions exposed by the micro-windows.

The polarization resistances varied widely for both austenite and ferrite and independently of the exposed area. Possibly differences due to crystalline orientation but these experiments demonstrated ability to make the electrochemical measurement on SMP samples.

EXAMPLE 6

Effect of the Size of the Exposed Area on the Current Measurements

The area exposed on the sample following development of the photoresist was determined using a numerical integration algorithm in the Alicona Infinite Focus Microscope image analysis routine.

For measurements conducted using a Gamry Series G 750 potentiostat, which can detect changes as small as 0.01 pA and has a leakage current of around 5 pA, the experimental set-up had a low-current limit of approximately 100 pA—regardless of the type of exposed phase. This translated into an exposed-area limit of no less than $3.0 \times 10^{-4}$ cm². For measurements conducted using a Gamry Reference 600 potentiostat, with its correspondingly better sensitivity, the practical exposed area limit was roughly $1.0 \times 10^{-4}$ cm².

Once the size of the exposed area decreased, the potentiostat began to be affected by the ambient electromagnetic noise in the room and was eventually unable to resolve the corrosion current throughout the entire polarization scan, thus setting the lowest limit of exposed area for making measurements.

EXAMPLE 7

Austenite Phase Results

In order to perform DC electrochemical experiments on individual phases of known crystalline orientation, we mapped cells in the surface grid using the EBSD camera to obtain the orientations of the various phases and identify the grains to be tested. The phase regions that had similar orientations within a cell were then laser processed and developed prior to undergoing a polarization scan in deaerated seawater. The polarization scan from a test on a single region of the austenite phase with a (111) orientation was demonstrated. Polarization scans from a selection of austenite phase regions with their respective crystalline orientations were also demonstrated.

EXAMPLE 8

Ferrite Phase Results

The polarization scan from a test on a single region of the ferrite phase with a (203) orientation in deaerated seawater was demonstrated. Polarization scans from a selection of ferrite phase regions with their respective crystalline orientations were also demonstrated.

EXAMPLE 9

Electrochemical Impedance Spectroscopy

In this section, the impedance behavior of the ferrite and austenite phases in seawater is presented in contrast to the behavior of the bulk alloy in seawater. The impedance tests were carried out in 50 mV increments from −400 $mV_{SCE}$ to +1000 $mV_{SCE}$. The AC potentials were ±10 mV RMS and the frequencies ranged from $1 \times 10^{5}$ to $1 \times 10^{-2}$ Hz at each potential. Nyquist plots for austenite, ferrite, and the bulk alloy at 5 different potentials were demonstrated.

Assuming that the oxide film impedance can be modeled using a solution resistance in series with a parallel circuit of a polarization resistance and constant phase element, then the depth of the electrically active region of the oxide film can be determined using Equation 1.

$$C_{dl} = \frac{1}{Z_{CPE}} = \frac{\epsilon \epsilon_0 A}{L} \qquad 1$$

where $C_{dl}$ is the double-layer capacitance, $\in_0$ is the free-space permittivity=$8.85 \times 10^{-14}$ F/cm, $\in$ is the dielectric constant for the oxide film—assumed to be about 15.6, A is the exposed area, and L is the depth of the active region of the oxide film.

The measured currents of the polarization curves suggest that at potentials below −400 mV$_{SCE}$, the oxide film is removed from the surface by the cathodic polarization but above −400 mV$_{SCE}$ to about +200 mV$_{SCE}$, the film covers the active surface and begins to thicken. Above +200 mV$_{SCE}$, even though the surface is still passive, the electro-active region of the film decreases, suggesting that the film is thinning or depleting a more active metal ion from the film. Above +400 mV$_{SCE}$, it appears as if another anodic reaction begins to dominate the dissolution process, but above +850 mV$_{SCE}$, that reaction is exhausted. Above +950 mV$_{SCE}$, the current rapidly begins rising as oxygen evolution begins and the oxide film is dissolving as quickly as it is formed.

EXAMPLE 10

Critical Pitting Temperature

At room temperature in seawater, neither austenite nor ferrite in 2205 is susceptible to pitting. The phases in these samples had estimated Pitting Resistance Equivalent Numbers (PREN) of 30.4 for the austenite and 36.16 for the ferrite. However, as the temperature of the seawater bath was elevated, metastable pitting events were observed above 45° C. with pitting occurring in ferrite around 61° C. and in austenite around 63° C. These tests do show that SMP can be used to make Critical Pitting Temperature measurements.

Using the SMP technique to mask off the untested areas of the 2205 samples allowed polarization scans to be performed at slow scan rates and without the concern of corrosion products obstructing the current path.

The high oven temperature and long, ~60 minute baking times for the photoresist inhibited the development of crevice corrosion under the photoresist at the edges of the exposed regions.

The corrosion current was directly related to the dimensions of the exposed area of the sample so that it was possible to expose and develop an area that had a corrosion current that was too low to be measured by the available potentiostats.

Polarization resistance dominated the current path with values range from $10^6$ ohms to $10^9$ ohms, with the solution resistance a manageable value of a few hundred ohms, as compared to solution resistances on the order of $10^3$ ohms for a microcapillary of similar dimensions.

The relatively low solution resistance allowed us to perform impedance measurements on the individual phases.

Alloy 2205 is a passive alloy that does not pit at room temperature in seawater but its oxide film does break down at very anodic potentials. Both phases exhibited a passive current density on the order of $10^{-6}$ A/cm$^2$ under anodic polarization between the open-circuit potential and a secondary dissolution peak around +0.5 V$_{SCE}$, followed by another region of passivity above the secondary dissolution peak before evolving oxygen. However, as was shown above, as the temperature of the sample was increased, stable pitting was observed in both phases. Plots were demonstrated for the potential at which the corrosion current density exceeded $10^{-4}$ A/cm$^2$ versus temperature for each phase and shows that ferrite and austenite behave quite differently at temperatures between 60° C. and 65° C. This is consistent with earlier observations showing that metastable pitting is different in austenite and ferrite and further demonstrates the ability to use SMP to obtain information on specific grains.

Results obtained from using the SMP technique suggest there are differences in the behavior of the passive films as a function of potential and temperature, indicating that phase composition plays a role in the corrosion resistance of the alloy. Another step concerns the differences in corrosion behavior due to crystalline orientation and phase. For one example, polarization curves for austenite and ferrite with similar crystalline orientations were demonstrated.

The results obtained from using the SMP technique demonstrate that it can be used to perform DC and AC electrochemical experiments on surface regions with an exposed area of <$10^{-4}$ cm$^2$—including irregularly-shaped regions such as cross-sectional areas of the dendrite fingers of the austenite phase in the 2205 duplex stainless steel.

The area that can be interrogated is related to the current sensitivity of the potentiostat.

Although the application for this disclosure concerns corrosion, SMP has wide applicability to any electrochemical study that explores the behavior of individual phase or isolated regions of interest.

Using SMP, differences in the impedance behavior of the oxide films and the transition to stable pitting above the critical pitting temperature have been investigated for ferrite and austenite regions in a duplex stainless steel. The results also indicate crystalline orientation probably does not play a role in the passive current density.

Some of the many advantages of this process over the previous ones are selection of the exact feature to be measured ahead of time and the ability to conduct slow potentiodynamic tests without compromising the sample or losing signal information because of solution resistance.

Many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What we claim is:

1. A method for isolating microstructural regions or features on a surface for electrochemical experimentation consisting of:
   providing a metal sample;
   coating the metal sample with a photoresist;
   selecting a region of interest on the metal sample;
   exposing the region of interest with light and creating exposed photoresist and unexposed photoresist with direct modulation of the light distribution itself by optoelectronic devices such as spatial light modulators or digital micromirror devices; and
   immersing the metal sample in a developer solution and removing the exposed photoresist and creating a developed region of unexposed photoresist.

2. The method for isolating microstructural regions of claim 1 further including the step of revealing the bare metal surface of the region of interest while protecting the developed region of unexposed photoresist.

3. The method for isolating microstructural regions of claim 2 further including the steps of hard-baking the metal sample and improving the coating reliability and adhesion and electrically isolating the developed region of unexposed photoresist.

4. The method for isolating microstructural regions of claim 3 further including the steps of polishing the metal sample prior to coating the metal sample with a photoresist and placing a grid reference mark on the metal sample prior to the step of selecting a region of interest of the metal sample.

5. The method for isolating microstructural regions of claim 4 wherein the step of placing a grid reference mark is by laser machining.

6. The method for isolating microstructural regions of claim 5 further including the steps of placing a water-resistant adhesive strip with a first perforated window over the region of interest and sealing a waterproof container with a second larger perforated window over the first perforated window and conducting electrochemical measurements.

7. The method for isolating microstructural regions of claim 3 utilizing a 1 μm-thick layer of photoresist via spin-coating onto the metal sample.

8. The method for isolating microstructural regions of claim 7 further including the step of soft-baking at 110° C. for about 1-2 minutes on a hot plate.

9. The method for isolating microstructural regions of claim 8 wherein the light is UV laser light and utilizing a laser energy of about 2.6 μJ corresponding to a fluence of about 200 mJ/cm$^2$.

10. The method for isolating microstructural regions of claim 9 utilizing a UV laser light that is a 355 nm solid state laser with maximum pulse energies of about 300 μJ and pulsewidths of about 30 ns.

11. The method for isolating microstructural regions of claim 3 utilizing a hard-baking step at a temperature of about 150° C. for about 60 minutes.

12. The method for isolating microstructural regions of claim 1 wherein the light can be pulsed or continuous.

13. The method for isolating microstructural regions of claim 2 wherein the light is UV laser light.

14. A method for isolating microstructural regions or features on a surface for electrochemical experimentation consisting of:
  providing a metal sample;
  coating the metal sample with a negative photoresist and thereby isolating the metal sample;
  selecting regions of interest on the metal sample;
  exposing the regions of interest with light energy and creating regions of exposed negative photoresist and regions of unexposed negative photoresist via utilizing a laser energy of about 2.6 microJoules corresponding to a fluence of about 200 mJ/cm$^2$ and a UV laser light that is a 355 nm solid state laser with maximum pulse energies of about 300 μJ and pulsewidths of about 30 ns with direct modulation of the light distribution itself by opto-electronic devices such as spatial light modulators or digital micromirror devices;
  immersing the metal sample in a developer solution and removing the regions of unexposed negative photoresist and creating developed regions of remaining photoresist and revealing bare steel surface of the regions of interest while protecting the regions of exposed negative photoresist; and
  hard-baking the metal sample and improving the coating reliability and adhesion and electrically isolating the developed regions of remaining negative photoresist.

* * * * *